(12) United States Patent
Miao

(10) Patent No.: US 8,822,669 B2
(45) Date of Patent: Sep. 2, 2014

(54) MIRNA EXPRESSION VECTOR

(71) Applicant: Xiangyang Miao, Beijing (CN)

(72) Inventor: Xiangyang Miao, Beijing (CN)

( * ) Notice: Subject to any disclaimer, the term of this patent is extended or adjusted under 35 U.S.C. 154(b) by 0 days.

(21) Appl. No.: 14/034,535

(22) Filed: Sep. 23, 2013

(65) Prior Publication Data

US 2014/0020126 A1    Jan. 16, 2014

Related U.S. Application Data

(63) Continuation-in-part of application No. PCT/CN2011/001322, filed on Aug. 10, 2011.

(30) Foreign Application Priority Data

Mar. 23, 2011    (CN) .......................... 2011 1 0070667

(51) Int. Cl.
   *A61K 48/00*    (2006.01)
   *C07H 21/02*    (2006.01)
   *C07H 21/04*    (2006.01)
   *C12N 15/11*    (2006.01)

(52) U.S. Cl.
   USPC ....................................... 536/24.5; 514/44 A

(58) Field of Classification Search
   USPC .......................................... 514/44; 536/24.5
   See application file for complete search history.

*Primary Examiner* — Terra Cotta Gibbs

(74) *Attorney, Agent, or Firm* — Matthias Scholl P.C.; Matthias Scholl

(57) ABSTRACT

A miRNA expression vector including SEQ ID NO. 11. The vector is capable of improving the fertility of animals by inhibiting the expression of inhibin.

4 Claims, 13 Drawing Sheets

SEQUENCE LISTING

<160> NUMBER OF SEQ ID NOS: 11

<210> SEQ ID NO 1
<211> LENGTH: 64
<212> TYPE: DNA
<213> ORGANISM: Artificial Sequence
<220> FEATURE:
<223> OTHER INFORMATION: Fully synthetic

<400> SEQUENCE: 1
tgctgtggaa agagatattg agggcggttt tggccactga ctgaccgccc tcaatctctt    60
tcca                                                                64

<210> SEQ ID NO 2
<211> LENGTH: 64
<212> TYPE: DNA
<213> ORGANISM: Artificial Sequence
<220> FEATURE:
<223> OTHER INFORMATION: Fully synthetic

<400> SEQUENCE: 2
cctgtggaaa gagattgagg gcggtcagtc agtggccaaa accgccctca atatctcttt    60
ccac                                                                64

<210> SEQ ID NO 3
<211> LENGTH: 64
<212> TYPE: DNA
<213> ORGANISM: Artificial Sequence
<220> FEATURE:
<223> OTHER INFORMATION: Fully synthetic

<400> SEQUENCE: 3
tgctgagtag aagatgaaac taggaggttt tggccactga ctgacctcct agtcatcttc    60
tact                                                                64

<210> SEQ ID NO 4
<211> LENGTH: 64
<212> TYPE: DNA
<213> ORGANISM: Artificial Sequence
<220> FEATURE:
<223> OTHER INFORMATION: Fully synthetic

<400> SEQUENCE: 4
cctgagtaga agatgactag gaggtcagtc agtggccaaa acctcctagt ttcatcttct    60
actc                                                                64

<210> SEQ ID NO 5
<211> LENGTH: 64
<212> TYPE: DNA
<213> ORGANISM: Artificial Sequence
<220> FEATURE:
<223> OTHER INFORMATION: Fully synthetic

<400> SEQUENCE: 5
tgctgagagt aacctccatc cgaggtgttt tggccactga ctgacacctc ggagaggtta    60
ctct                                                                64

<210> SEQ ID NO 6
<211> LENGTH: 64
<212> TYPE: DNA
<213> ORGANISM: Artificial Sequence
<220> FEATURE:
<223> OTHER INFORMATION: Fully synthetic

```
<400> SEQUENCE: 6
cctgagagta acctctccga ggtgtcagtc agtggccaaa acacctcgga tggaggttac    60
tctc                                                                 64

<210> SEQ ID NO 7
<211> LENGTH: 64
<212> TYPE: DNA
<213> ORGANISM: Artificial Sequence
<220> FEATURE:
<223> OTHER INFORMATION: Fully synthetic

<400> SEQUENCE: 7
tgctgttaga tgcaagcaca gtgctggttt tggccactga ctgaccagca ctgcttgcat    60
ctaa                                                                 64

<210> SEQ ID NO 8
<211> LENGTH: 64
<212> TYPE: DNA
<213> ORGANISM: Artificial Sequence
<220> FEATURE:
<223> OTHER INFORMATION: Fully synthetic

<400> SEQUENCE: 8
cctgttagat gcaagcagtg ctggtcagtc agtggccaaa accagcactg tgcttgcatc    60
taac                                                                 64

<210> SEQ ID NO 9
<211> LENGTH: 64
<212> TYPE: DNA
<213> ORGANISM: Artificial Sequence
<220> FEATURE:
<223> OTHER INFORMATION: Fully synthetic

<400> SEQUENCE: 9
tgctgaaatg tactgcgcgt ggagacgttt tggccactga ctgacgtctc cacgcagtac    60
attt                                                                 64

<210> SEQ ID NO 10
<211> LENGTH: 64
<212> TYPE: DNA
<213> ORGANISM: Artificial Sequence
<220> FEATURE:
<223> OTHER INFORMATION: Fully synthetic

<400> SEQUENCE: 10
cctgaaatgt actgcgtgga gacgtcagtc agtggccaaa acgtctccac gcgcagtaca    60
tttc                                                                 64

<210> SEQ ID NO 11
<211> LENGTH: 21
<212> TYPE: DNA
<213> ORGANISM: Artificial Sequence
<220> FEATURE:
<223> OTHER INFORMATION: Fully synthetic

<400> SEQUENCE: 11
acctcggatg gaggttactc t                                              21
```

MIRNA EXPRESSION VECTOR

CROSS-REFERENCE TO RELATED APPLICATIONS

This application is a continuation-in-part of International Patent Application No. PCT/CN2011/001322 with an international filing date of Aug. 10, 2011, designating the United States, now pending, and further claims priority benefits to Chinese Patent Application No. 201110070667.5 filed Mar. 23, 2011. The contents of all of the aforementioned applications, including any intervening amendments thereto, are incorporated herein by reference. Inquiries from the public to applicants or assignees concerning this document or the related applications should be directed to: Matthias Scholl P.C., Attn.: Dr. Matthias Scholl Esq., 14781 Memorial Drive, Suite 1319, Houston, Tex. 77079

BACKGROUND OF THE INVENTION

1. Field of the Invention

The invention relates to the construction of a vector, and more particularly to a miRNA expression vector for improving the fertility of animals.

2. Description of the Related Art

Inhibin (INH) can specifically inhibit the pituitary cells from synthesizing and secreting follicle-stimulating hormone (FSH), and thus affects the maturation and development of the ovarian follicle in the ovary. Inhibin includes an α-subunit and a β-subunit which are connected by disulfide bonds. Only when the α subunit and the β subunit are integrated in vivo, the inhibin shows the bioactivity.

Studies show there is a close relationship between the α-subunit of the inhibin and the reproductive performance of animals. Insert 1-32 segments of the α-subunit into the carboxyl terminal of HBsAg-S to yield a DNA vaccine of the inhibin. 40 sheep were vaccinated by the DNA vaccine and the twin percentage thereof was measured. The results showed that the vaccinated group had an obviously higher twin percentage (39.2%) than a control group (the twin percentage was 10%) ($P<0.05$). Thus, the specific immunization targeting the inhibin by using the DNA vaccine induces the development of more ovarian follicles, thereby improving the fertility. Other studies also show that through the active immunization against the inhibin, antibodies of the inhibin are induced in animals, the inhibition of the endogenous inhibin on the synthesis and release of the FSH is relieved, thereby improving the fertility of animals. However, the active immunization against the inhibin works only in parental generations, the character of high fertility cannot be passed on to filial generations, and thus it is not a long-term mechanism.

miRNA is between 21 and 25 nt in length, and is originated from processing an endogenous transcript precursor pri-miRNA which is between 70 and 90 nt in length and is capable of forming a hairpin structure. miRNA is highly conservative in evolution. The specific complementary base pairing between miRNA and mRNA can degrade the mRNA or inhibit the translation of the mRNA, so miRNA plays an important role in gene regulations. The constituted-in-vitro miRNA expression vector targeting specific genes can effectively inhibit the expression of corresponding genes. Lentivirus, with lower transfection permission (both dividing cells and nondividing cells can be transfected) and higher transfection efficiency, is widely used for the regulations of gene expression.

SUMMARY OF THE INVENTION

In view of the above-described problems, it is one objective of the invention to provide an interference vector capable of improving the fertility of animals.

To achieve the above objective, in accordance with one embodiment of the invention, there is provided a miRNA lentivirus vector, comprising SEQ ID NO. 11.

The vector can inhibit the expression of inhibin of sheep. The vector is transfected into cells to generate miRNA comprising SEQ ID NO. 11, thus the translation of the mRNA of the inhibin of the sheep is inhibited, whereby inhibiting the expression of the inhibin proteins.

The miRNA lentivirus vector is mixed with a liposome and trypan blue to yield a transfection solution. The transfection solution is injected into testis of sheep from multipoints by using a minimally invasive surgery. The transfected sheep is mated with female counterparts to give birth to ten female F1 generations having positive character. The female F1 generations are selected for breeding experiments, and the results show that the twin percentage thereof is significantly improved in contrast with non-transgenic sheep.

The vector can be used for developing new sheep varieties having high fertility. Because the vector inhibits the expression of the inhibin protein of sheep, the inhibition of the endogenous inhibin on the synthesis and release of the FSH is relieved, thereby improving the fertility of animals, which lays the foundation for developing new sheep varieties.

In accordance with another embodiment of the invention, there provided is a pMD-18T vector, comprising SEQ ID NO. 6.

BRIEF DESCRIPTION OF THE DRAWINGS

The invention is described hereinbelow with reference to accompanying drawings, in which.

DETAILED DESCRIPTION OF THE EMBODIMENTS

Figure 1A:
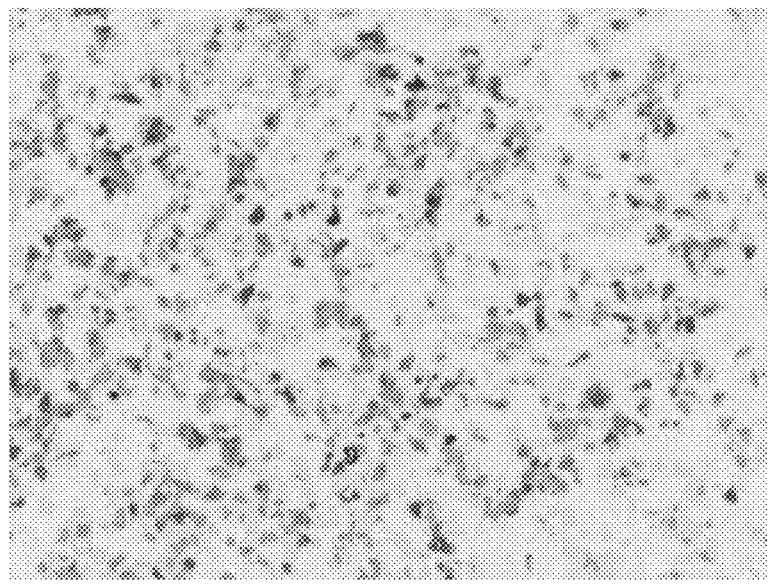
FIG. 1A shows a photo of cotransfected HEK293 (200×) by an interference plasmid No. MR062-1 and an INHA high expression plasmid under a fluorescence vision.
Figure 1B:
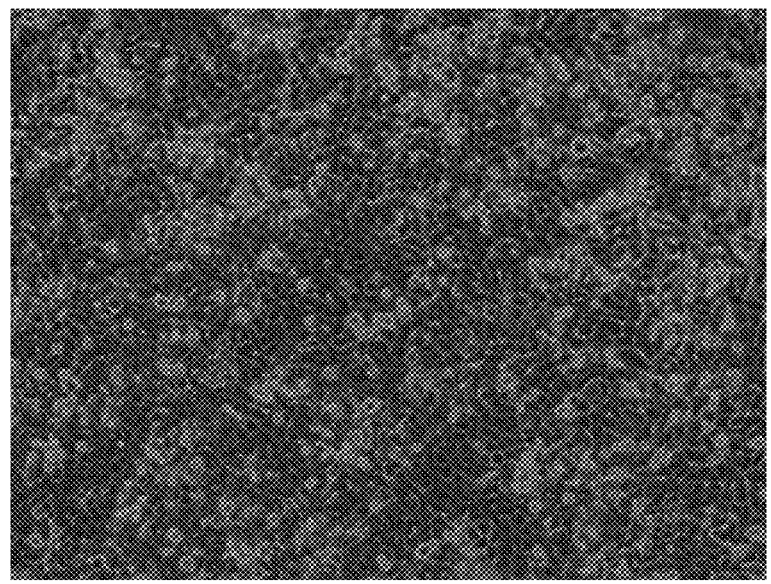
FIG. 1B shows a photo of cotransfectedHEK293 (200×) by an interference plasmid No. MR062-1 and an INHA high expression plasmid under visible light.
Figure 2A:
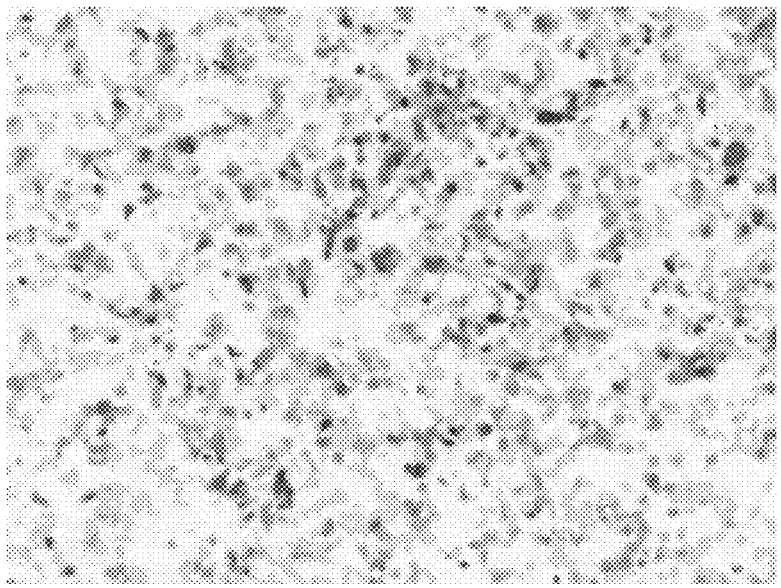
FIG. 2A shows a photo of cotransfectedHEK293 (200×) by an interference plasmid No. MR062-2 and an INHA high expression plasmid under a fluorescence vision.
Figure 2B:
FIG. 2B shows a photo of cotransfectedHEK293 (200×) by an interference plasmid No. MR062-2 and an INHA high expression plasmid under visible light.
Figure 3A:
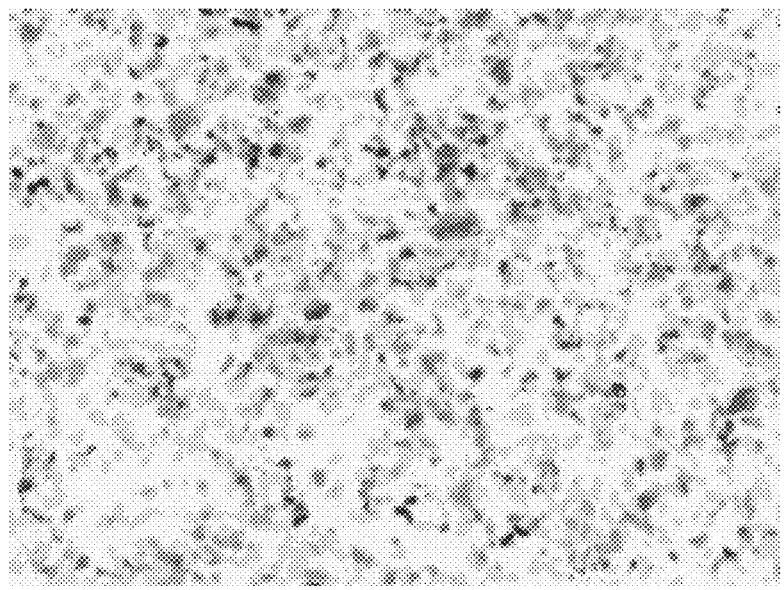
FIG. 3A shows a photo of cotransfectedHEK293 (200×) by an interference plasmid No. MR062-3 and an INHA high expression plasmid under a fluorescence vision.
Figure 3B:
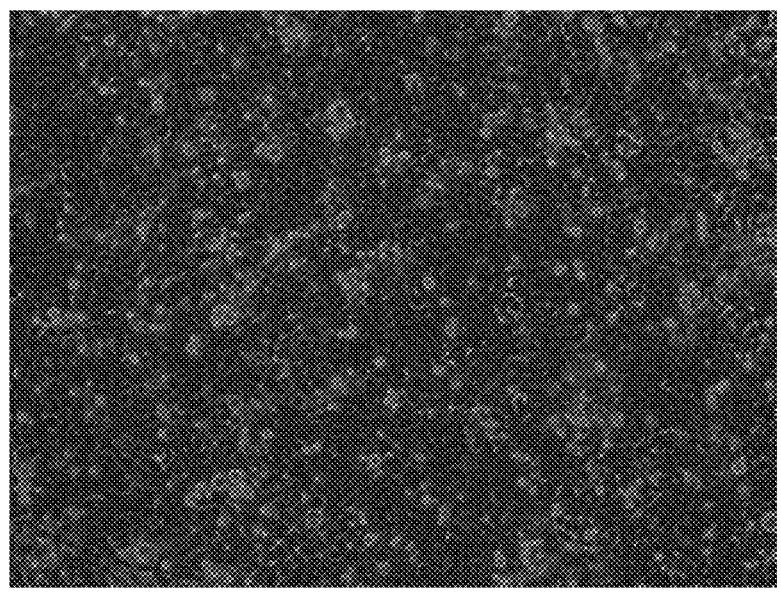
FIG. 3B shows a photo of cotransfectedHEK293 (200×) by an interference plasmid No. MR062-3 and an INHA high expression plasmid under visible light.
Figure 4A:
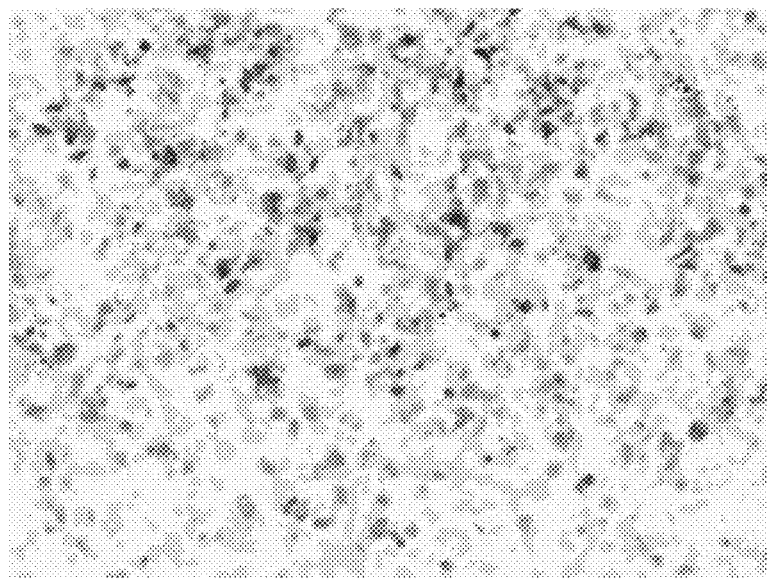
FIG. 4A shows a photo of cotransfectedHEK293 (200×) by an interference plasmid No. MR062-4 and an INHA high expression plasmid under a fluorescence vision.
Figure 4B:
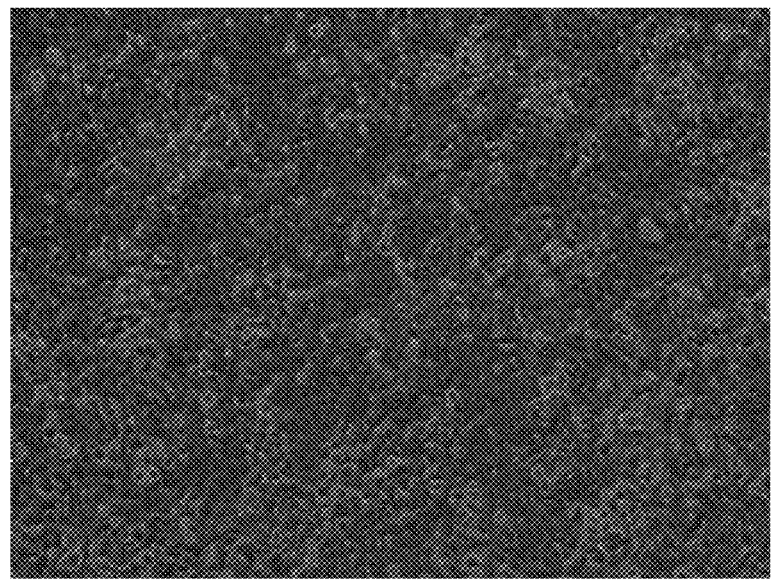
FIG. 4B shows a photo of cotransfectedHEK293 (200×) by an interference plasmid No. MR062-4 and an INHA high expression plasmid under visible light.
Figure 5A:
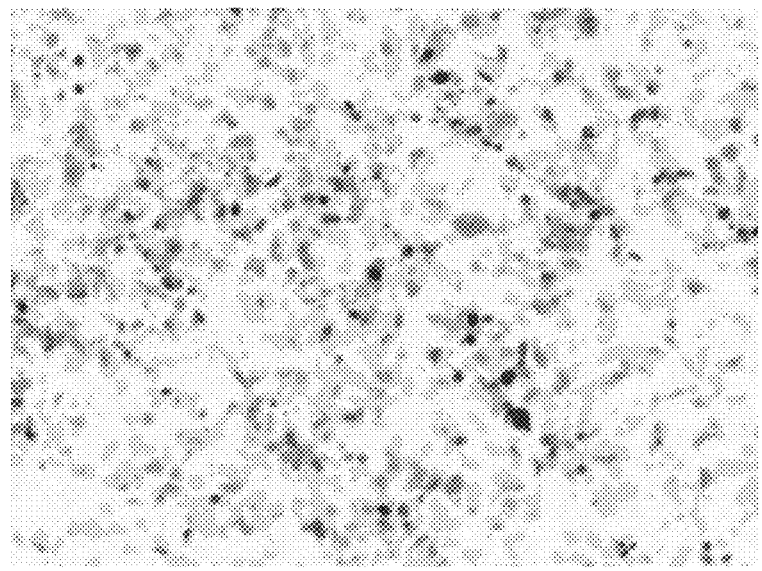
FIG. 5A shows a photo of cotransfectedHEK293 (200×) by SR-neg negative control plasmid and an INHA high expression plasmid under a fluorescence vision.
Figure 5B:
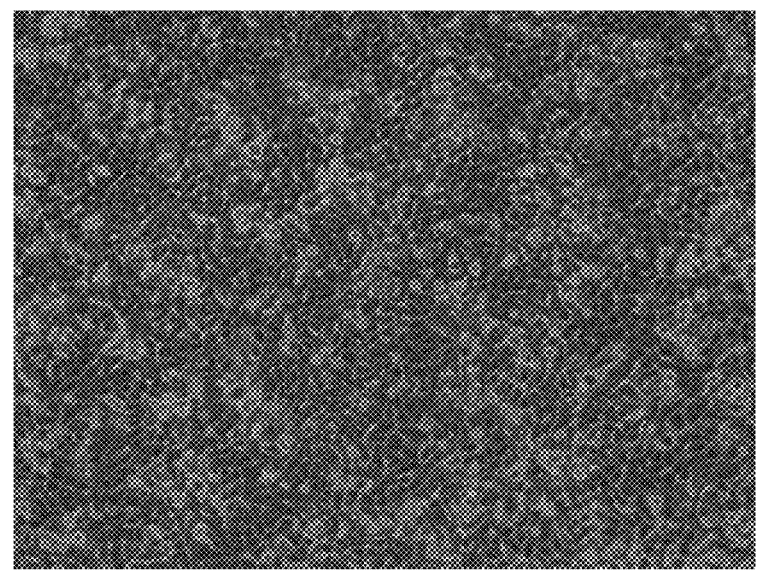
FIG. 5B shows a photo of cotransfectedHEK293 (200×) by SR-neg negative control plasmid and an INHA high expression plasmid under visible light.
Figure 6A:
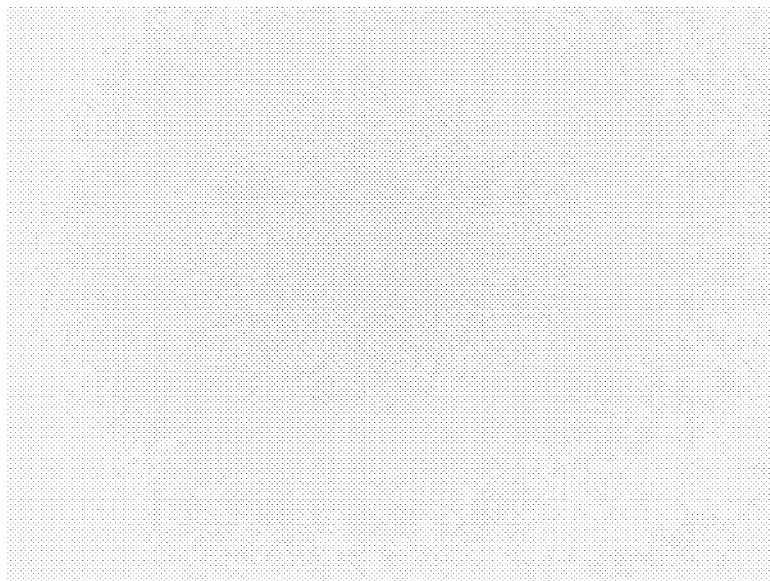
FIG. 6A shows a photo of transfected HEK293 (200×) by a blank control plasmid under a fluorescence vision.
Figure 6B:
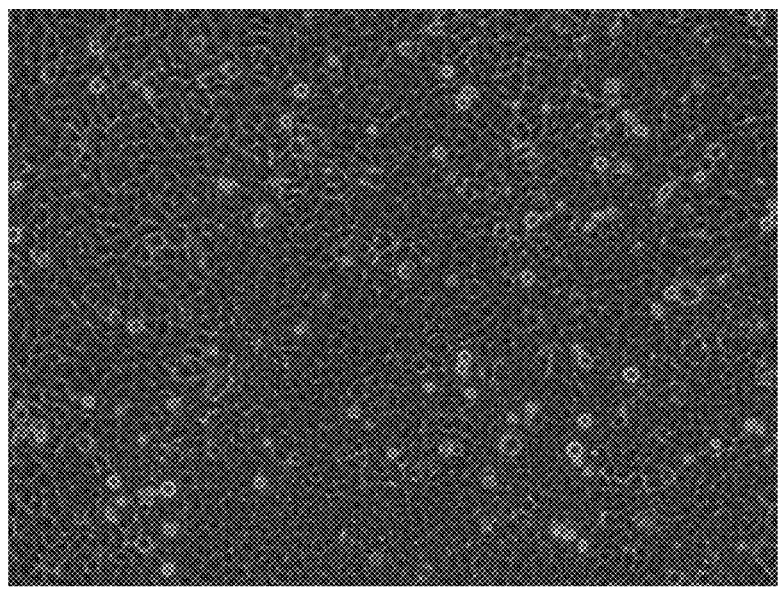
FIG. 6B shows a photo of transfected HEK293 (200×) by a blank control plasmid under visible light.

For further illustrating the invention, experiments detailing a miRNA lentivirus vector for improving the fertility of animals are described below. It should be noted that the following examples are intended to describe and not to limit the invention.

Example 1

Part 1: Research Method

1. Construction of miRNA Interference Vector

Online miRNA design tool (http://rnaidesigner.invitrogen.com/rnaiexpress/) provided by Invitrogen Corporation was utilized to synthesize 4 pairs of miRNA single-stranded oligonucleotides (as shown in Table 1) according to a nucleotide sequence of sheep INHA gene (L28815).

TABLE 1

Sequences of miRNA oligo (underlined fonts are interference target sequences)

| Olig names | | DNA sequence of Single-stranded oligo from 5' to 3' |
|---|---|---|
| MR062-1-F | SEQ ID NO. 1 | TGCTGTGGAAAGAGATATTGAGGGCGGTTTTG GCCACTGACTGACCGCCCTCAATCTCTTTCCA |
| MR062-1-R | SEQ ID NO. 2 | CCTGTGGAAAGAGATTGAGGGCGGTCAGTCA GTGGCCAAAAC<u>CGCCCTCAATATCTCTTTCCAC</u> |
| MR062-2-F | SEQ ID NO. 3 | TGCTGAGTAGAAGATGAAACTAGGAGGTTTTG GCCACTGACTGACCTCCTAGTCATCTTCTACT |
| MR062-2-R | SEQ ID NO. 4 | CCTGAGTAGAAGATGACTAGGAGGTCAGTCAG TGGCCAAAAC<u>CTCCTAGTTTCATCTTCTACTC</u> |
| MR062-3-F | SEQ ID NO. 5 | TGCTGAGAGTAACCTCCATCCGAGGTGTTTTG GCCACTGACTGACACCTCGGAGAGGTTACTCT |
| MR062-3-R | SEQ ID NO. 6 | CCTGAGAGTAACCTCTCCGAGGTGTCAGTCAG TGGCCAAAAC<u>ACCTCGGATGGAGGTTACTCTC</u> |
| MR062-4-F | SEQ ID NO. 7 | TGCTGTTAGATGCAAGCACAGTGCTGGTTTTG GCCACTGACTGACCAGCACTGCTTGCATCTAA |
| MR062-4-R | SEQ ID NO. 8 | CCTGTTAGATGCAAGCAGTGCTGGTCAGTCAG TGGCCAAAAC<u>CAGCACTGTGCTTGCATCTAAC</u> |
| Negative-F | SEQ ID NO. 9 | tgctgAAATGTACTGCGCGTGGAGACGTTTTGGC CACTGACTGACGTCTCCACGCAGTACATTT |
| Negative-R | SEQ ID NO. 10 | cctgAAATGTACTGCGTGGAGACGTCAGTCAGT GGCCAAAAC<u>CGTCTCCACGCGCAGTACATTT</u>c |

4 pairs of the synthesized miRNA single-stranded oligonucleotides were respectively dissolved in ddH$_2$O to yield solutions having a concentration of 100 μM, 5 μL, of each of the complementary single strands were mixed to form a mixed solution, respectively, and annealed. 4 mixed solutions were heated at the temperature of 95° C. for 5 min, and naturally cooled at the room temperature for 20 min to form double-stranded oligos, respectively. The double-stranded oligos after being annealed was diluted to a concentration of 10 nM, and vector construction kit BLOCK-iT™ Pol II miR- RNAi Expression Vector Kit with EmGFP was used to insert 4 pairs of the double-stranded miRNA oligos into miRNA expression vector pcDNA™6.2-GW/EmGFPmiR, respectively; and connection were performed at the room temperature for 30 min. 4 miRNA expression plasmids were constructed and transformed DH5α competent cells. 3 clones were picked from each transformation plate and sequenced to verify whether the fragment sequence inserted into recombinant clones were consistent to the designed oligo sequences.

2. Construction of INHA Expression Vector

Complete sequence analysis was performed on coding region of the INHA gene to test whether particularly complicate secondary structures and repetitive sequences exist in the gene sequence. According to results from gene sequence analysis, single-stranded oligos were designed and synthesized, and sticky ends were formed on two terminals of the sequence. The oligos were assembled to form a complete gene by PCR. The synthesized sequence was carried by pMD-18T vector and was used to transform DH5α competent cells. Genome of the transformed DH5α competent cells were sequenced to verify whether the fragment sequence inserted into recombinant clones met the requirements. Mutations in genome sequence were repaired by overlap PCR. Mutated full length fragment were cut with enzyme XhoI and EcoRI, connected to the target vector pIRES2-eGFP, and were used to transform DH5α competent cells. Sequence information of target gene fragment in recombinant clones were tested to obtain a correct INHA efficient expression vector.

3. Screen of Interference Vector

1) Cell Transfection

HEK293 cells in good growing condition were dissociated, counted, and inoculated to a 6-well plate with $5\times10^5$ cells per well. When the cells were grown in a stable state and a fusion rate was approximately 80%, transfection experiment was conducted. Cells in a bottom of the well were washed by a serum-free Opti-MEM once, and added with 1.5 mL of the Opti-MEM. Each of 3 ug of interference plasmid MR062-1, MR062-2, MR062-3, MR062-4, negative control plasmid SR-neg, and 1 ug of efficient expression plasmid was diluted with 250 uL of the Opti-MEM to form a mixed solution, and the mixed solution was evenly mixed. 10 uL of a Lipofectamine 2000 reagent was diluted by 250 uL of the Opti-MEM; a mixture was mixed gently and cultured at the room temperature for 5 min. The diluted plasmid and the Lipofectamine 2000 dilution were mixed and stayed at the room temperature for 20 min. 500 uL of lipid-plasmid complexes were added to and evenly mixed with cells in each well, respectively. The 6-well plate was transferred to a 5% $CO_2$ incubator for culturing for 4-6 h. Thereafter, an original culturing solution was replaced by a complete culturing solution (not containing antibiotic), and the 6-well plate was continued to be cultured in the 5% $CO_2$ incubator overnight at the temperature of 37° C. Fluorescence expression was observed on a second morning.

2) qPCR Detection

Total RNA in transformed HEK293 cells was extracted by Trizol method, and reversely transcribed to yield cDNA which was then detected by q-PCR. q-PCR comprised a 50 uL reaction system, and the reaction conditions were as follows: 95° C. for 2 min; 95° C. for 10 min, 60° C. for 20 s, and 72° C. for 30 s, the above three steps were repeated for 40 cycles; and 72° C. for 10 min; the temperature was maintained for 30 s after increasing by every 0.5° C. from 60° C., after 70 cycles, the temperature climbed to 95° C. Finally, gene expression level and silencing efficiency of the target gene were calculated by the following methods:

$\Delta\Delta ct$=(an average ct of the target gene of the sample to be tested–an average ct of the housekeeping gene of the sample to be tested)–(an average ct of the target gene of the control sample–an average ct of the housekeeping gene of the control sample)

Gene expression level $F=2^{-\Delta\Delta ct}$; and silencing efficiency of the target gene was $1-2^{\Delta\Delta ct}$.

4. Construction of Lentivirus Vector

BP recombination system provided by Invitrogen Corporation was utilized: a BP recombination system comprising 2 uL of pcDNA™6.2-GW/EmGFPmi-SR (60-150 ng), 1 uL of pDONR221 vector, 2 uL of BP Clonase II, and 5 uL of ultra-pure water was allowed to react at the temperature of 25° C. for 1 h. Thereafter, 1 uL of proteinase K was added to the BP recombination system, and a recombination solution was allowed to react at the temperature of 37° C. for 10 min 100 uL of DH5α competent cells were transformed with 5 uL of the recombination reaction solution, positive clones were selected and tested by sequencing, and BP recombination plasmid that was tested to be correct by sequencing was collected. Therefore, miRNA expressed sequence was recombined on pDONR221vector.LR recombination system provided by Invitrogen Corporation was utilized: a LR recombination system comprising 1 uL of BP recombination plasmid produced from the BP recombination, 1 uL of pLenti6.3/V5-DEST, 2 uL of LR Clonase II, and 6 uL of ultra-pure was allowed to react at the temperature of 25° C. for 1 h. After that, 1 uL of proteinase K was added to the LR recombination system, and a recombination solution was allowed to react at the temperature of 37° C. for 10 min 100 uL of Stb13 competent cells were transformed with 5 uL of the recombination reaction solution, positive clones were selected and tested by sequencing, and BP recombination plasmid that was tested to be correct by sequencing was collected. Thus, miRNA expressed sequence was recombined on pLenti6.3/V5-DEST lentivirus vector.

5. Preparation of Lentivirus 293T cells in good growing condition and in logarithmic phase were collected, digested, and counted. Each 10 cm cell culture dish was inoculated with $3\times10^6$ cells, and was cultured at the temperature of 37° C. overnight in the $CO_2$ incubator. 9 ug of Packaging Mix and 3 ug of recombined lentivirus plasmid were added to 1.5 mL of Opti-MEM to form a first solution; 36 ul of Lipofectamine2000 was added to 1.5 mL of Opti-MEM to form a second solution. The first solution and the second solution were stayed at the room temperature for 5 min, respectively. After that, the first solution and the second solution were evenly mixed and incubated at the room temperature for 20 min to form a plasmid-liposome DNA complex. Cells in the cell culture dish were washed by Opti-MEM twice, and then 5 mL of Opti-MEM was added. 3 mL of plasmid-liposome DNA complex was added to the cell culture dish, a resulting mixture was evenly mixed, and incubated in the $CO_2$ incubator at the temperature of 37° C. for between 4 and 6 h. Thereafter, culture medium was replaced. After being cultured for 48 h, a first supernatant of cell culturing solution was collected and centrifuged at a speed of 3000 rpm for 15 min Cell residue was removed, a second supernatant was filtered by a 0.45 um filter, each tube was filled with 1.0 mL of the second supernatant. Lentivirus was persevered at the temperature of –80° C.

6. Lentivirus Titer Determination

On a first day, cells were dissociated by trypsin, counted, inoculated to a 24-well plate, and incubated at the temperature of 37° C. overnight. The cell fusion rate was between 30% and 50% during infection. On a second day, to conduct cell transfection, lentivirus solution was defrozen, diluted by a culture medium comprising 2% FBS by a method of 10-fold serial dilution from $10^{-1}$ to $10^{-6}$ (each concentration gradient was repeated twice). In serial dilution of lentivirus, the previous dilution was slightly decanted to be mixed with the culture medium to form a lentivirus dilute solution, and vortex mixing was not employed herein. Original culture medium in the 24-well plate was removed. Each tube of lentivirus dilute solution was slightly decanted, and 1 mL of the lentivirus dilute solution was collected and added to cells in each well. Polybrene was added to the well until a concentration thereof was 8 ug/mL, and evenly mixed. The cells were cultured at the temperature of 37° C. overnight. On a third day, the culture medium comprising lentivirus was removed, and 2 mL of complete medium was added. On a fourth or a fifth day, GFP expression in each well was observed under a fluorescence microscope, and lentivirus titer (TU)/mL was determined according to the following formula:

$$\frac{(\text{average number of positive cells/visual field}) \times (\text{number of visual fields/well})}{\text{volume of } lentivius \text{ (mL)} \times \text{dilution folds}}$$

Part 2: Results

Figure 7:
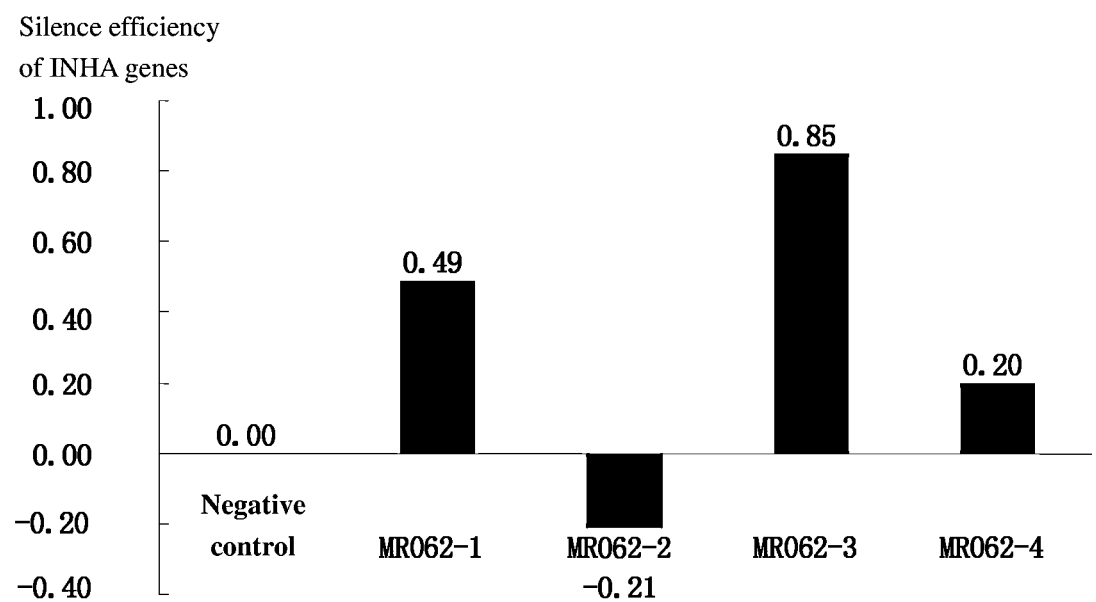
FIG. 7 shows a silence efficiency of an interference plasmid on INHA genes.
Figure 8A:
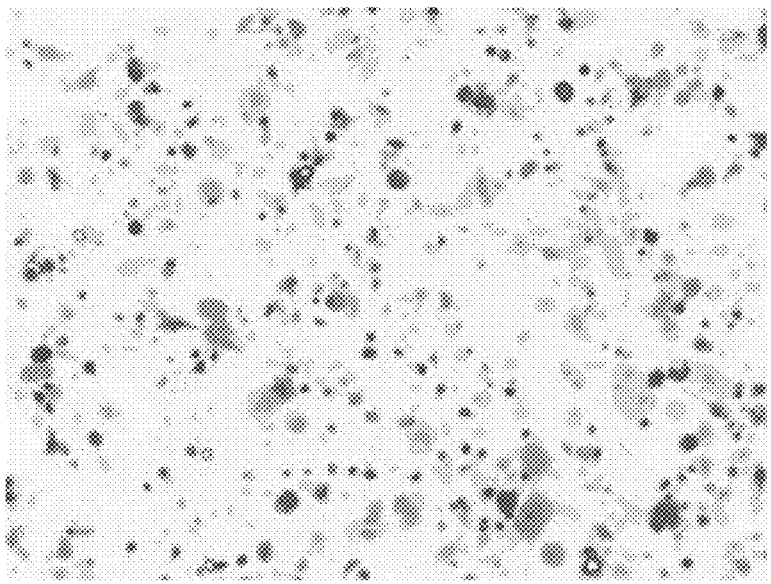
FIG. 8A shows cells (200×) after 48 h of virus packaging of a lentivirus interference plasmid No. MR062-3 under a fluorescence vision.
Figure 8B:
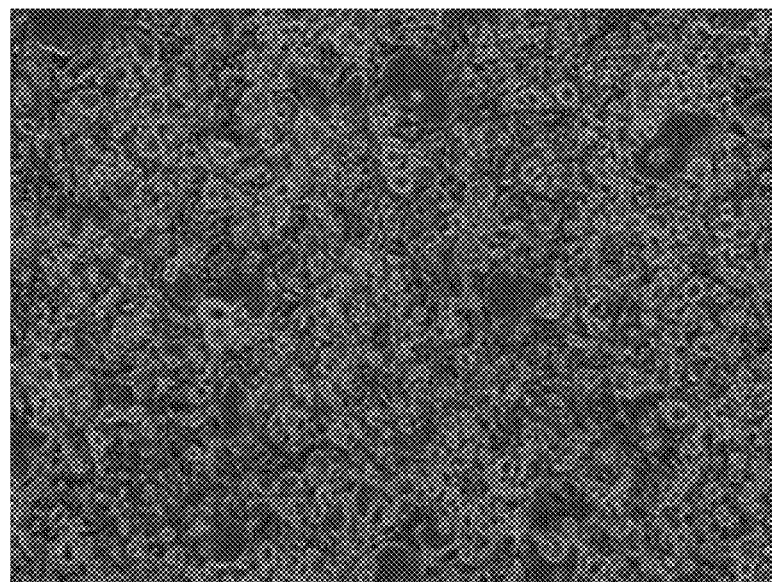
FIG. 8B shows cells (200×) after 48 h of virus packaging of a lentivirus interference plasmid No. MR062-3 under visible light.
Figure 9A:
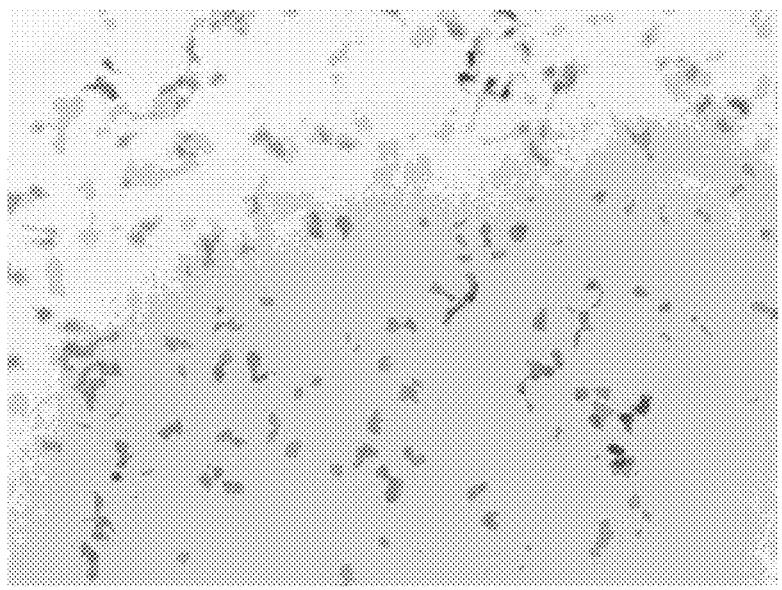
FIG. 9A shows positive expression (200×) when a virus concentrate is diluted for $10^3$ times under a fluorescence vision.
Figure 9B:
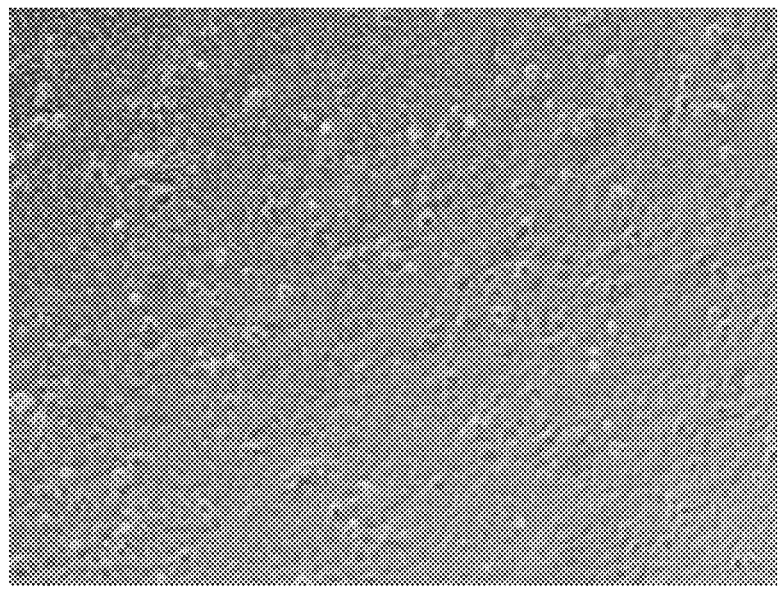
FIG. 9B shows positive expression (200×) when a virus concentrate is diluted for $10^3$ times under visible light.
Figure 10A:
FIG. 10A shows positive expression (200×) when a virus concentrate is diluted for $10^4$ times under a fluorescence vision.
Figure 10B:
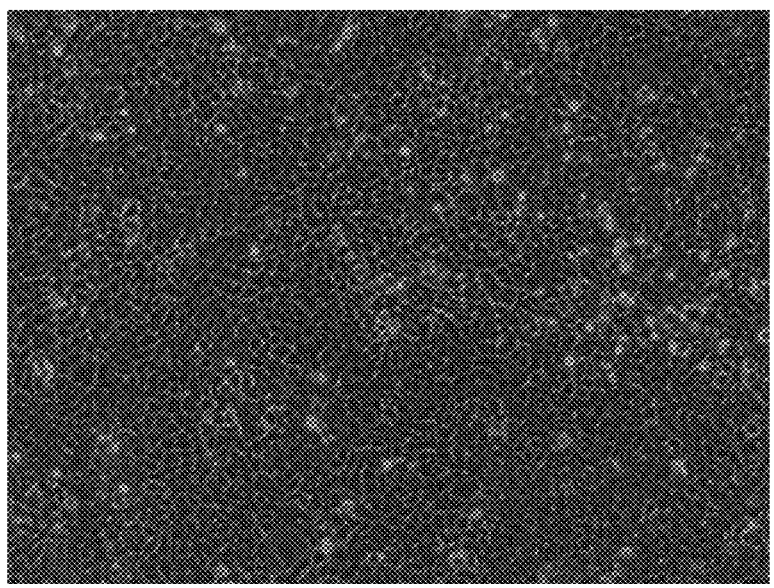
FIG. 10B shows positive expression (200×) when a virus concentrate is diluted for $10^4$ times under visible light.
Figure 11A:
FIG. 11A shows positive expression (200×) when a virus concentrate is diluted for $10^5$ times under a fluorescence vision.
Figure 11B:
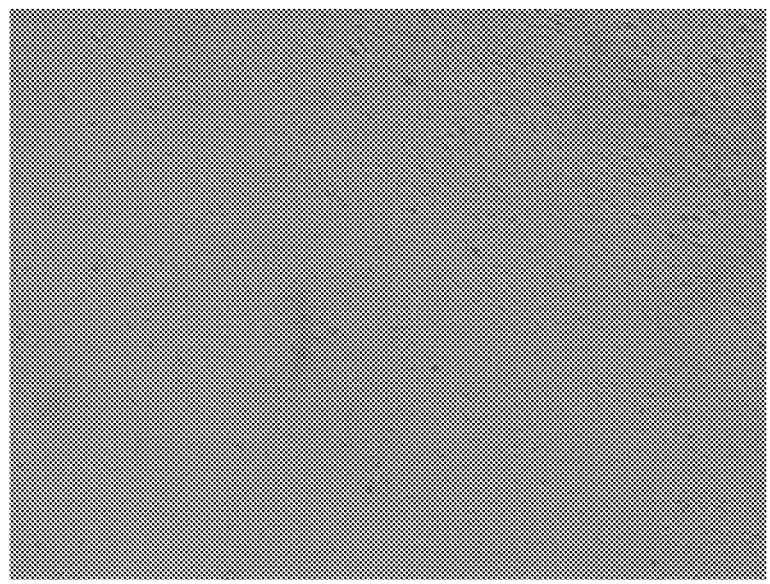
FIG. 11B shows positive expression (200×) when a virus concentrate is diluted for $10^5$ times under visible light.
Figure 12A:
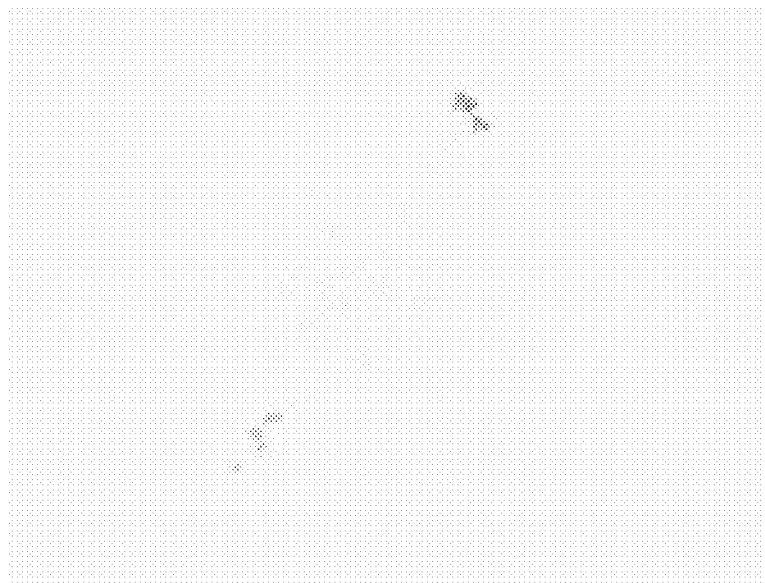
FIG. 12A shows positive expression (200×) when a virus concentrate is diluted for $10^6$ times under a fluorescence vision.
Figure 12B:
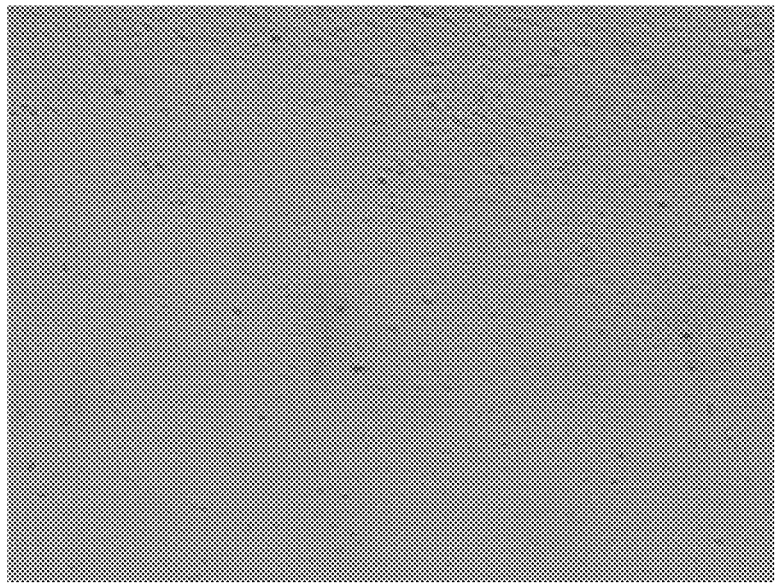
FIG. 12B shows positive expression (200×) when a virus concentrate is diluted for $10^6$ times under visible light.

It was known from the sequencing that miRNA expression vector was successfully constructed; INHA efficient expression vector was successfully constructed. Results from the q-PCR detection shown that, expression of the target gene INHA was higher than the background (as shown in Table 2) in cells transfected by efficient expression plasmid pIRES2-EGFP-INHA. The HEK293 cells were transfected by the constructed miRNA expression vector and INHA efficient expression vector, and were screened; results were observed under the fluorescence microscope, as shown in FIGS. 1-6. From q-PCR detection, it was found that MR062-3 interference plasmid has the highest interference efficiency, as shown in Table 3, the silencing efficiency of the target gene was approximately 85%. Silencing efficiencies of INHA gene in cells transfected by the negative control plasmid SR-neg and interference plasmid MR062-1, MR062-2, MR062-3, and MR062-4 were shown in FIG. 7. MR062-3 interference plasmid was used to construct lentivirus interference plasmid, and results from the sequencing indicated that the lentivirus interference plasmid was successfully constructed. After package of the lentivirus plasmid, a lentivirus solution having a titer of $3.18 \times 10^7$ TU/mL was obtained. Results from observation under the fluorescence microscope during the lentivirus titer determination were shown in FIGS. 8-12.

TABLE 2

Results of q-PCR detection of efficient expression plasmid

| | Ct (target gene) | Ct (Actin) | ΔCt | ΔΔCt | $2^{-\Delta\Delta Ct}$ |
|---|---|---|---|---|---|
| Background | 32.66 | 13.83 | 18.83 | 0 | 1 |
| Efficient expression transfection | 10.92 | 22.07 | −11.15 | −29.98 | 1058959303 |

Detection results indicated that expression of target gene INHA was higher than the background by $10^{10}$ in cells transfected by efficient expression plasmid pIRES2-EGFP-INHA.

TABLE 3

Results of q-PCR detection of HEK293 cells transfected by interference plasmid and efficient expression plasmid

| | Ct (target gene) | Ct (Actin) | ΔCt | ΔΔCt | $2^{-\Delta\Delta Ct}$ |
|---|---|---|---|---|---|
| Negative control | 10.92 | 22.07 | −11.15 | 0 | 1 |
| MR062-1 | 11.18 | 21.37 | −10.19 | 0.96 | 0.514056913 |
| MR062-2 | 12.78 | 24.21 | −11.43 | −0.28 | 1.214194884 |
| MR062-3 | 13.6 | 22.03 | −8.43 | 2.72 | 0.151774361 |
| MR062-4 | 12.81 | 23.64 | −10.83 | 0.32 | 0.801069878 |

MR062-3 interference plasmid has the best interference effect, and is approximated to 84.82%. Sequence of MR062-3-R (SEQ ID NO. 6) was CCTGAGAGTAA CCTCTC-CGAG GTGTCAGTCA GTGGCCAAAA CACCTCGGAT GGAGGTTACTCTC, in which, a primary sequence for realizing the function of the interference plasmid was ACCTCG-GATGG AGGTTACTCT (SEQ ID NO. 11). The invention constructed the MR062-3 interference plasmid of miRNA lentivirus vector against α-subunit of sheep inhibin; the MR062-3 interference plasmid had an obvious inhibition effect on the expression level of the inhibin and was a basis for improving fertility of new sheep varieties.

Example 2

Application of Lentivirus Vector in Sheep Breeding 28 male sheep were provided. INHA lentivirus interference expression vector, liposome, and trypan blue were mixed to form a transfection solution. Thereafter, the transfection solution was multi-point injected into sheep testicles on both sides by minimally invasive surgery, the male sheep were mated with female sheep. INHA gene expression in F1 generation was detected by PCR. False-positive F1 generation lambs were eliminated by Southern blotting. 11 positive male F1 generation lambs and 10 positive female F1 generation lambs were obtained.

Figure 13:
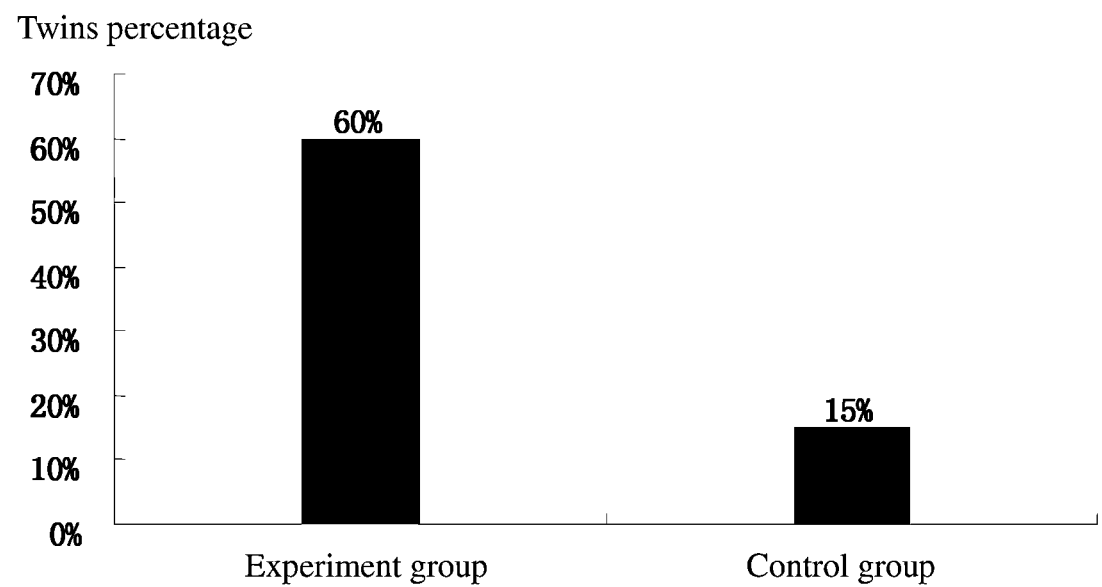
FIG. 13 shows twin percentages of transgenic sheep and non-transgenic sheep. The experiment group employs female sheep having low expression of inhibin, and the control group employs non-transgenic sheep.

Breeding experiments were performed on the positive female F1 generation sheep. The experiment had two groups, in which, an experiment group was that 10 positive female F1 generation sheep were mated with non-transgenic male sheep, and a control group was that 20 pairs of transgenic sheep were mated. Twin percentages of the two groups were compared (as shown in FIG. 13), it was known from the results that the twin percentage of the experiment group was 60% (6/10), and the twin percentage of the control group was 15% (3/20). Lentivirus vector transgenic animal experiment indicated that INHA lentivirus interference expression vector was capable of significantly improving the fertility of animals.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. A miRNA expression vector, comprising SEQ ID NO. 11.

2. A method for inhibiting expression of sheep inhibin, the method comprising transfecting the miRNA expression vector of claim 1 into sheep cells to generate a miRNA comprising SEQ ID NO. 11 and to inhibit translation of mRNA of sheep inhibin.

3. A method for developing a sheep variety using the miRNA expression vector of claim 1, the method comprising
   mixing the miRNA expression vector of claim 1 with liposome and trepan blue to yield a transfection solution;
   injecting the transfection solution into a testicle of a male sheep;
   breeding the male sheep with a female sheep to obtain female F1 generation sheep;
   selecting the female F1 generation sheep that express inhibin α-subunit gene to develop the sheep variety.

4. A pMD-18T vector, comprising SEQ ID NO. 6.

* * * * *